(12) United States Patent
Hickey et al.

(10) Patent No.: US 6,310,166 B1
(45) Date of Patent: Oct. 30, 2001

(54) STERILIZED CYANOACRYLATE SOLUTIONS CONTAINING THICKENERS

(75) Inventors: Timothy Hickey, Raleigh; Ubonwan A. Stewart, Durham, both of NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/374,207

(22) Filed: Aug. 12, 1999

(51) Int. Cl.$^7$ ...................................................... C08F 10/14
(52) U.S. Cl. .................................... 526/348.2; 526/348.3; 526/348.4; 523/503; 523/118; 522/152; 522/173; 522/77
(58) Field of Search ............................. 526/348.2, 348.3, 526/348.4; 522/152, 173, 77; 523/118

(56) References Cited

U.S. PATENT DOCUMENTS

| | | |
|---|---|---|
| Re. 32,889 | 3/1989 | Litke . |
| 2,721,858 | 10/1955 | Joyner et al. . |
| 3,254,111 | 5/1966 | Hawkins et al. . |
| 3,527,841 | 9/1970 | Wicker, Jr. et al. . |
| 3,554,990 | 1/1971 | Quinn et al. . |
| 3,559,652 | 2/1971 | Banitt et al. . |
| 3,564,078 | 2/1971 | Wicker, Jr. et al. . |
| 3,940,362 | 2/1976 | Iverhults . |
| 3,961,966 | 6/1976 | Brinkmann et al. . |
| 3,995,641 | 12/1976 | Kronenthal et al. . |
| 4,035,334 | 7/1977 | Dauvdov et al. . |
| 4,038,345 | 7/1977 | O'Sullivan et al. . |
| 4,127,382 | 11/1978 | Perry . |
| 4,170,585 * | 10/1979 | Motegi et al. ...................... 260/33.2 |
| 4,313,865 | 2/1982 | Teramoto et al. . |
| 4,364,876 | 12/1982 | Kimura et al. . |
| 4,378,213 | 3/1983 | Severy . |
| 4,477,607 | 10/1984 | Litke . |
| 4,529,384 | 7/1985 | Severy . |
| 4,533,422 | 8/1985 | Litke . |
| 4,550,041 | 10/1985 | Thompson et al. . |
| 4,560,723 | 12/1985 | Millet et al. . |
| 4,636,539 | 1/1987 | Harris et al. . |
| 4,720,513 | 1/1988 | Kameyama et al. . |
| 4,749,730 | 6/1988 | Jimenez . |
| 4,793,888 | 12/1988 | Card et al. . |
| 4,804,691 | 2/1989 | English et al. . |
| 4,844,102 | 7/1989 | Repensek et al. . |
| 5,259,835 | 11/1993 | Clark et al. . |
| 5,328,687 | 7/1994 | Leung et al. . |
| 5,350,798 | 9/1994 | Linden et al. . |
| 5,514,371 | 5/1996 | Leung et al. . |
| 5,514,372 | 5/1996 | Leung et al. . |
| 5,530,037 | 6/1996 | McDonnell et al. . |
| 5,575,997 | 11/1996 | Leung et al. . |
| 5,582,834 | 12/1996 | Leung et al. . |
| 5,589,554 | 12/1996 | Hiraoka . |
| 5,624,669 | 4/1997 | Leung et al. . |
| 5,654,010 | 8/1997 | Johnson et al. . |
| 5,665,817 | 9/1997 | Greff et al. . |
| 6,038,464 * | 3/2000 | Axelgaard et al. ...................... 600/391 |
| 6,103,778 | 8/2000 | Hyon et al. . |
| 6,143,805 * | 11/2000 | Hickey et al. ...................... 522/152 |

FOREIGN PATENT DOCUMENTS

| | | |
|---|---|---|
| 0 824 867 A1 | 2/1998 | (EP) . |
| 63-273679 | 3/1989 | (JP) . |
| WO 99/18950 | 4/1999 | (WO) . |

OTHER PUBLICATIONS

Tseng et al., "Physical Modification of α–Cyanoacrylate for Application as Surgical Adhesives," *Progress in Biomedical Polymers*, 1990, pp. 53–63.

Tseng et al., "Effect of Poly(D,L–lactide) Addition to 2–Cyanoacrylates on Their Physical and Toxicity," *Journal of Bioactive and Compatible Polymers*, vol. 4, 1989, pp. 101–109.

Tseng et al., "Medical Application of Cyanoacrylates as Surgical Adhesives—Effects of Thickened Cyanoacrylates on Healing of Skin Wounds—,"*Jpn. J. Artif. Organs,* vol. 18, No. 1, 1989, pp. 409–413.

Chemical Abstract 110:63675 (Polym. Mater. Sci. Eng., 59, 911–15, 1988).

Chemical Abstract 111:63893 (Jinko Zoki, 18(1), 409–13, 1989).

Chemical Abstract 111:102669 (J. Bioact. Compat. Polym., 4(2), 101–9, 1989).

Chemical Abstract 112:104774 (J. Biomed. Mater. Res., 24(1), 65–77, 1990).

Chemical Abstract 114:150130 (Prog. Biomed. Polm., [Proc. Am. Chem. Soc. Symp.], 1998, 53–63.

* cited by examiner

*Primary Examiner*—David W. Wu
*Assistant Examiner*—William Cheung

(57) ABSTRACT

A method of making a sterile adhesive composition includes placing a mixture of a polymerizable adhesive monomer and a thickening agent in a container, sealing the container, and sterilizing the mixture and the container. The method provides superior viscosity for the monomer composition. The sterile adhesive composition is particularly useful as a medical adhesive and can comprise 1,1-disubstituted ethylene monomers, such as α-cyanoacrylates.

7 Claims, No Drawings

STERILIZED CYANOACRYLATE SOLUTIONS CONTAINING THICKENERS

BACKGROUND OF THE INVENTION

1. Field of the Invention

The invention relates to sterilized monomer and polymer adhesive and sealant compositions, and to their production for industrial and medical uses.

2. State of the Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate and an adjunct to surgical sutures and staples in wound closure as well as for covering and protecting surface wounds such as lacerations, abrasions, burns, stomatitis, sores, and other open surface wounds. When an adhesive is applied to surfaces to be joined, it is usually applied in its monomeric form, and the resultant polymerization gives rise to the desired adhesive bond. However, at ordinary temperatures, the monomeric form runs when applied to surfaces. As a result, the monomeric adhesive may spread into a wound or along a surface to areas that do not require an adhesive. Therefore, the monomeric form must be controlled in order to prevent undue escape of the adhesive from any given area to which the adhesive is applied. Additionally, sufficient time must be allowed for the monomeric material to polymerize and thus to bring about the desired bonding action. In order to achieve a suitably viscous adhesive, thickening agents can be added to the monomer compositions.

For example, U.S. Pat. No. 3,527,841 to Wicker et al. discloses α-cyanoacrylate adhesive compositions for both general and surgical uses containing a viscosity modifier that is soluble, after heating, in a wide range of the esters of α-cyanoacrylic acid. The viscosity modifier is disclosed as poly(lactic acid). After addition of the poly(lactic acid), the composition is sterilized at temperatures up to 150° C. Most of the resulting compositions experienced a decrease in viscosity, presumably resulting from degradation of the thickener by the sterilization process.

U.S. Pat. No. 5,665,817 to Greff et al. discloses alkyl cyanoacrylate compositions suitable for topical application to human skin. The compositions may comprise a suitable amount of a thickening agent to provide a compositional viscosity suitable for certain applications onto human skin. The thickening agent is added to provide a viscosity of from about 2 to 50,000 centipoise at 20° C. The thickening agent employed is any biocompatible material that increases the viscosity of the alkyl cyanoacrylate composition and includes, by way of example, a partial polymer of the alkyl cyanoacrylate, polymethylmethacrylate (PMMA), or other preformed polymers soluble in the alkyl cyanoacrylate. When these solutions are to be stored in applicators suitable for repeated intermittent use, the alkyl cyanoacrylate composition is stored at ambient conditions and is selected to be bacteriostatic. When the selected composition is bacteriostatic, prolonged storage at ambient conditions is without regard to the sterility of the formulation because there is no adverse buildup of bacteria during storage.

U.S. Pat. No. 5,328,687 to Leung et al. also discloses adhesive compositions that may be used for bonding tissue. Compositions comprising α-cyanoacrylate monomers are preferred. The compositions may further contain adjuvant substances such as thickening agents. Suitable disclosed thickeners include, for example, polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Without specific reference to thickened or unthickened compositions, the '687 patent also mentions that compositions employed in the invention are sterilizable by conventional methods such as by autoclave or by aseptic filtration techniques.

In addition to being viscous, cyanoacrylate compositions for use in many medical applications should be sterile. Due to the importance of achieving and maintaining sterility of these compositions, when an additive, such as a thickening agent, is added to an α-cyanoacrylate composition, it should be added prior to sterilazation. A problem arises because some thickeners require pretreatment prior to addition to the monomer compositions. U.S. Pat. No. 4,038,345 to O'Sullivan et al. discloses stable cyanoacrylate adhesive compositions having viscosities greater than about 200 centipoise. The compositions are prepared by incorporating, as a thickening agent, a soluble acrylic polymer having a reduced viscosity of about 5 or greater, and a content of free radical polymerization initiator less than 1% by weight. These properties are obtained by subjecting the thickening agent to temperatures of about 140–180° C. for about 30–180 minutes prior to incorporating it in the cyanoacrylate. In one aspect, the '345 patent concerns a process for preparing improved cyanoacrylates which involves heating a conventional polyacrylate thickener at a suitable temperature and for a suitable period of time to reduce its content of free radical polymerization initiators to below about one percent, and increase its reduced viscosity to greater than 5; and dissolving a sufficient amount of the thickener in an ester of 2-cyanoacrylic acid to produce a cyanoacrylate adhesive composition having a viscosity of at least about 500 centipoise. The most highly preferred thickening compound is poly(methylmethacrylate). This thickener is incorporated into the cyanoacrylate monomer by stirring to form a solution. In preparing the thickener, it is maintained at an elevated temperature for a suitable period of time. A satisfactory temperature range is between about 140° and 180° C., and a satisfactory time period is from about 30 to 180 minutes.

However, regardless of the type and number of additives, sterilization of α-cyanoacrylate adhesive compositions is often difficult to achieve. For example, widely practiced methods of sterilization, such as dry and moist heat sterilization, ionizing radiation, exposure to gas, and sterile filtration, are often not suitable for use with monomeric cyanoacrylate compositions. Problems arise due to polymerization of the monomer during the sterilization process. In many cases, sterilization-induced polymerization is so severe that the resulting product is unusable.

Methods currently used to package and sterilize α-cyanoacrylate monomer compositions have been developed with the recognition that, to improve efficiency and productivity, the packaging and sterilizing steps should be performed in rapid succession. However, these methods do not provide the desired viscosity of the adhesive compositions. For example, U.S. Pat. No. 5,530,037 to McDonnell et al. discloses that the composition of a sterilezed adhesive would be very limited because necessary additives could not be conveniently added and mixed in a controlled fashion. For example, viscosity modifiers such as polymethylmethacrylate (PMMA) would require heating in a separate vessel to achieve dissolution and this step would destroy the sterility.

Additionally, the problem exists that some thickeners decompose in electron beam and dry heat sterilization. One example of this is poly(2-octylcyanoacrylate), which degrades when exposed to a 160° C. dry heat sterilization cycle or 20–30 kGy of electron beam radiation. In order to confirm this, formulations were prepared using poly(2-octylcyanoacrylate) as a thickening agent and 2-octylcyanoacetate as the non-polymerizable medium. The data in Table I confirms that poly(2-octylcyanoacrylate) is unstable under current dry heat and electron beam sterilization methods.

TABLE I

Poly(2-octylcyanoacrylate)(P2OCA)
P2OCA Thickened Formulations

Viscosity (cps)

| Run # | Control | 160° C. Dry Heat | % Change | 20 kGy | % Change | 30 kGy | % Change |
|---|---|---|---|---|---|---|---|
| 1 | 117 | 31 | −73.2 | 37 | −68.3 | 31 | −73.5 |
| 2 | 138 | 62 | −55.2 | 46 | −67.0 | 37 | −73.2 |
| 3 | 133 | 48 | −64.2 | 36 | −73.0 | 32 | −73.9 |
| 4 | 139 | 63 | −54.7 | 43 | −69.1 | 37 | −73.4 |
| 5 | 139 | 64 | −53.9 | 40 | −71.2 | 35 | −74.8 |
| 6 | 143 | 57 | −60.1 | 45 | −68.3 | 38 | −73.4 |
| 7 | 142 | 70 | −50.4 | 40 | −71.6 | 33 | −76.8 |
| 8 | 142 | 67 | −53.1 | 44 | −68.8 | 38 | −73.2 |

Visocosity is used as a measure of stability since a stable formulation should have a viscosity change of zero after sterilization. If the viscosity decreases, this indicates degradation of the thickener (here, poly(2-octylcyanoacrylate)).

Many other thickeners are also subject to decomposition under sterilization conditions. Such instability is particularly common in compositions in which the adhesive monomers are stabilized by the presence of acids, because those acids frequently destabilize the thickening polymers also present in the composition. For example, lactic acid-caprolactone copolymers in a stabilized 2-octylcyanoacrylate monomer composition tend to decompose when such a composition is subjected to dry heat sterilization conditions, causing the thickener to lose thickening effect. Such acid stabilizers are, however, present in many cyanoacrylate adhesive compositions.

In addition, aseptic filtration is a known method for sterilizing cyanoacrylate compositions before they are placed into a container. However, aseptic filtration is very difficult with high viscosity compositions, and involves prohibitively expensive technology.

Thus, a need exists for improved monomer cyanoacrylate adhesive compositions, especially for medical uses, having a greater viscosity without sacrificing the performance of the adhesive. The need further exists for a sterilized monomeric adhesive composition that does not require pre-treatment of the thickener prior to its addition to the monomeric adhesive. Additionally, the need exists for a sterilized monomeric adhesive in which the thickener has not decomposed during sterilization.

SUMMARY OF THE INVENTION

The present invention provides a method of making a thickened sterile monomeric adhesive composition. Production of the composition includes placing a mixture of a polymerizable 1,1-disubstituted ethylene monomer and a thickening agent in a container, sealing the container and sterilizing the container and the mixture. The thickening agent is soluble in the monomer at room temperature. The compositions produced, packaged and sterilized according to the present invention have greater viscosity, and extended utility, as compared to adhesive compositions of the prior art.

DETAILED DESCRIPTION OF PREFERRED EMBODIMENTS

According to the invention, a sterile viscous monomeric adhesive composition is manufactured by adding a thickening agent to a composition comprising a monomer adhesive prior to sterilization.

The thickening agents may be selected from among known thickeners, including, but not limited to, poly(2-ethylhexyl methacrylate), poly(2-ethylhexyl acrylate) and cellulose acetate butyrate. Suitable thickeners include, for example, polycyanoacrylates, polyoxalates, lactic-glycolic acid copolymers, polycaprolactone, lactic acid-caprolactone copolymers, poly(caprolactine+DL-lactide+glycolide), polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly (butylmethacrylate) and poly(butylacrylate), also copolymers of various acrylate and methacrylate monomers, such as poly(butylmethacrylate-co-methylmethacrylate). Biodegradable polymer thickeners are preferred for some uses such as some surgical uses. Preferably, the thickening agent is soluble in a monomer composition at room temperature (i.e., 20–25° C.) so that it may be added to the monomer composition without excessive heating of the monomer composition and remain uniformly combined in the composition.

The amount of thickening agent that is added to the monomer composition depends upon the molecular weight of the thickening agent. The thickening agent preferably comprises from about 0.5–25.0% by weight of the adhesive composition. In preferred embodiments, the thickening agent comprises from about 1.0–10.0%, more preferably 1.0–5.0%, of the adhesive composition. In embodiments, the thickening agent has a high molecular weight, preferably at least 100,000, or at least 500,000 or at least 1,000,000. The thickening agent is selected such that it is compatible with the monomer (i.e., does not adversely affect polymerization, bond strength, core properties, or shelf-life). The amount of thickening agent to be used can be determined by one of ordinary skill in the art using known techniques without undue experimentation.

In embodiments, the sterilized adhesive composition has a viscosity of about 20–500 centipoise, preferably 30–400 centipoise, as measured with a Brookfield Viscometer at 25° C. Additionally, the viscosity of the composition should be maintained or increased by a controlled and acceptable amount after sterilization.

According to embodiments of the present invention, the stability, and thus the shelf-life, of some monomeric adhesive compositions can be further enhanced and extended through carefull regulation of the packaging (i.e., dispensing into a container) and sterilizing procedures. In preferred embodiments, there is substantially no initiation of polymerization of monomeric liquid adhesive compositions that affects the utility of the monomer or monomers caused by the sterilization process. In particular, a polymerizable 1,1-disubstituted monomer and a thickening agent are dispensed into a container. The container is sealed and subjected to sterilization.

The monomeric composition may be packaged in any type of suitable container fabricated from materials including, but not limited to, glass, plastic, metal packages, and film-formed packages. Suitable containers are those into which the compositions can be dispensed and sterilized without unacceptable damage to, or degradation of, the container or the components of the monomer composition. Glass is especially preferred when sterilization is achieved with dry heat because of the lack of stability of many plastics at the temperatures used for dry heat sterilization (typically at least 160° C.). Examples of types of containers include, but are not limited to, ampoules, vials, syringes, pipettes, and the like. In a preferred embodiment, the container comprises a sealable container.

In embodiments, monomer compositions according to the invention are sterilized. The sterilization can be accomplished by techniques known to the skilled artisan, and is preferably accomplished by methods including, but not limited to, chemical, physical, and irradiation methods. Examples of chemical methods include, but are not limited to, exposure to ethylene oxide or hydrogen peroxide vapor. Examples of physical methods include, but are not limited to, sterilization by heat (dry or moist). Examples of irradiation methods include, but are not limited to, gamma irradiation, electron beam irradiation, and microwave irradiation. Preferred methods are dry and moist heat sterilization and electron beam sterilization. In embodiments where a composition is to be used for medical applications, the sterilized composition must show low levels of toxicity to living tissue during its useable life.

The sterilization conditions and thickeners should be selected in light of each other, and preferably also in light of other components of the composition. For example, in a highly acid stabilized composition, a less acid-unstable thickener and/or less degrading sterilization conditions would be preferable. Biodegradable polymer thickeners such as lactic acid-caprolactone copolymers, for example, better survive electron beam sterilization rather than dry heat sterilization in acid stabilized cyanoacrylate compositions. Where a biodegradable thickener is not required, on the other hand, a more acid-stable thickener such as poly(2-ethylhexyl) methacrylate may be used with, for example, dry heat sterilization. Thus, by taking into account the selection of the thickener and the selection of the sterilization conditions, along with the nature of the underlying composition, one of ordinary skill in the art can readily select appropriate parameters by routine experimentation to allow sterilization of a thickened adhesive composition in a container.

The monomer composition, in embodiments, is preferably a monomeric (including prepolymeric) adhesive composition. The monomer composition may further include one or more polymerizable monomers. In embodiments, at least one of the one or more monomers is a 1,1-disubstituted ethylene monomer, e.g., an α-cyanoacrylate. Preferred monomer compositions of the present invention, and polymers formed therefrom, are useful as tissue adhesives, sealants for preventing bleeding or for covering open wounds, and in other biomedical applications. They find uses in, for example, apposing surgically incised or traumatically lacerated tissues; retarding blood flow from wounds; drug delivery; dressing bums; dressing skin or other superficial or surface wounds (such as abrasions, chaffed or raw skin, and/or stomatitis); and aiding repair and regrowth of living tissue. Other preferred monomer compositions of the present invention, and polymers formed therefrom, are useful in industrial and home applications, for example in bonding rubbers, plastics, wood, composites, fabrics, and other natural and synthetic materials.

Monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. No. 5,328,687 to Leung, et al., which is hereby incorporated in its entirety by reference herein.

Useful 1,1-disubstituted ethylene monomers include, but are not limited to, monomers of the formula:

$$HRC=CXY \qquad (I)$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (I) include α-cyanoacrylates, vinylidene cyanides, C$_1$–C$_4$ alkyl homologues of vinylidene cyanides, dialkyl methylene malonates, acylacrylonitriles, vinyl sulfinates and vinyl sulfonates of the formula CH$_2$=CX'Y' wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are α-cyanoacrylates. These monomers are known in the art and have the formula

(II)

wherein R$^2$ is hydrogen and R$^3$ is a hydrocarbyl or substituted hydrocarbyl group; a group having the formula —R$^4$—O—R$^5$—O—R$^6$, wherein R$^4$ is a 1,2-alkylene group having 2–4 carbon atoms, R$^5$ is an alkylene group having 2–4 carbon atoms, and R$^6$ is an alkyl group having 1–6 carbon atoms; or a group having the formula

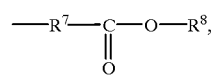

wherein $R^7$ is

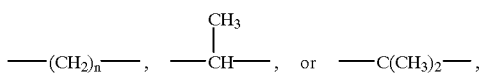

wherein n is 1–10, preferably 1–5 carbon atoms and $R^8$ is an organic moiety.

Examples of suitable hydrocarbyl and substituted hydrocarbyl groups include straight chain or branched chain alkyl groups having 1–16 carbon atoms; straight chain or branched chain $C_1$–$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1$–$C_8$ alkyl moieties, $C_2$–$C_8$ alkenyl moieties, $C_2$–$C_8$ alkynyl moieties, $C_3$–$C_{12}$ cycloaliphatic moieties, aryl moieties such as phenyl and substituted phenyl and aralkyl moieties such as benzyl, methylbenzyl, and phenylethyl. Other organic moieties include substituted hydrocarbon moieties, such as halo (e.g., chloro-, fluoro- and bromo-substituted hydrocarbons) and oxy-substituted hydrocarbon (e.g., alkoxy substituted hydrocarbons) moieties. Preferred organic radicals are alkyl, alkenyl, and alkynyl moieties having from 1 to about 8 carbon atoms, and halo-substituted derivatives thereof. Particularly preferred are alkyl moieties of 4 to 6 carbon atoms.

In the cyanoacrylate monomer of formula (II), $R^3$ is preferably an alkyl group having 1–10 carbon atoms or a group having the formula -$AOR^9$, wherein A is a divallent straight or branched chain alkylene or oxyalkylene moiety having 2–8 carbon atoms, and $R^9$ is a straight or branched alkyl moiety having 1–8 carbon atoms.

Examples of groups represented by the formula -$AOR^9$ include 1-methoxy-2-propyl, 2-butoxy ethyl, isopropoxy ethyl, 2-methol ethyl, and 2-ethoxy ethyl.

The α-cyanoacrylates of formula (II) can be prepared according to methods known in the art. U.S. Pat. Nos. 2,721,858 and 3,254,111, each of which is hereby incorporated in its entirety by reference, disclose methods for preparing α-cyanoacrylates. For example, the α-cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The α-cyanoacrylate monomers prepared with low moisture content and essentially free of impurities are preferred for biomedical use.

The α-cyanoacrylates of formula (II) wherein $R^3$ is a group having the formula $R^4$—O—$R^5$—O—$R^6$ can be prepared according to the method disclosed in U.S. Pat. No. 4,364,876 to Kimura et al., which is hereby incorporated in its entirety by reference. In the Kimura et al. method, the α-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The α-cyanoacrylates of formula (II) wherein $R^3$ is a group having the formula

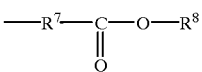

can be prepared according to the procedure described in U.S. Pat. No. 3,995,641 to Kronenthal et al., which is hereby incorporated in its entirety by reference. In the Kronenthal et al. method, such α-cyanoacrylate monomers are prepared by reacting an alkyl ester of an α-cyanoacrylic acid with a cyclic 1,3-diene to form a Diels-Alder adduct which is then subjected to alkaline hydrolysis followed by acidification to form the corresponding α-cyanoacrylic acid adduct. The α-cyanoacrylic acid adduct is preferably esterified by an alkyl bromoacetate to yield the corresponding carbalkoxymethyl α-cyanoacrylate adduct. Alternatively, the α-cyanoacrylic acid adduct may be converted to the α-cyanoacrylyl halide adduct by reaction with thionyl chloride. The α-cyanoacrylyl halide adduct is then reacted with an alkyl hydroxyacetate or a methyl substituted alkyl hydroxyacetate to yield the corresponding carbalkoxymethyl α-cyanoacrylate adduct or carbalkoxy alkyl α-cyanoacrylate adduct, respectively. The cyclic 1,3-diene blocking group is finally removed and the carbalkoxy methyl α-cyanoacrylate adduct or the carbalkoxy alkyl α-cyanoacrylate adduct is converted into the corresponding carbalkoxy alkyl α-cyanoacrylate by heating the adduct in the presence of a slight deficit of maleic anhydride.

Examples of monomers of formula (II) include cyanopentadienoates and α-cyanoacrylates of the formula:

wherein Z is —CH═$CH_2$ and $R^3$ is as defined above. The monomers of formula (III) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated in its entirety by reference.

Preferred α-cyanoacrylate monomers used in this invention are alkyl α-cyanoacrylates including octyl cyanoacrylate, such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. More preferred monomers are n-butyl and 2-octyl α-cyanoacrylate. Monomers utilized for medical purposes in the present application should be very pure and contain few impurities (e.g., surgical grade). Monomers utilized for industrial purposes need not be as pure.

The composition may optionally also include at least one plasticizing agent that imparts flexibility to the polymer formed from the monomer. The plasticizing agent preferably contains little or no moisture and should not significantly affect the stability or polymerization of the monomer. Such plasticizers are useful in polymerized compositions to be used for closure or covering of wounds, incisions, abrasions, sores or other applications where flexibility of the adhesive is desirable. Some thickeners, such as poly-2-ethylhexylcyanoacrylate, can also impart flexibility to the polymer.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts ranging from about 0.5 wt. % to about 25 wt. %, or from about 1 wt. % to about 20 wt. %, or from about 3 wt. % to about 15 wt.% or from about 5 wt. % to about 7 wt. % provides increased elongation and toughness of the polymerized monomer over polymerized monomers not having plasticizing agents.

The composition may also optionally include at least one thixotropic agent. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513, the disclosure of which is hereby incorporated in its entirety.

The composition may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. PAT. Nos. 4,313,865 and 4,560,723, the disclosures of which are hereby incorporated in their entireties.

The composition may also optionally include both at least one anionic vapor phase stabilizer and at least one anionic liquid phase stabilizer. These stabilizing agents inhibit polymerization. Such stabilizing agents may also include mixtures of anionic stabilizing agents and radical stabilizing agents. Any mixture of stabilizers is included as long as the mixture does not inhibit the desired polymerization of the monomer and is compatible with the selected thickener under the selected sterilization conditions, as discussed above.

The anionic vapor phase stabilizers may be selected from among known stabilizers, including, but not limited to, sulfur dioxide, boron trifluoride, and hydrogen fluoride. The amount of anionic vapor phase stabilizer that is added to the monomer composition depends on the identity of the liquid phase stabilizer(s) chosen in combination with it, the monomer to be stabilized, as well as the packaging material to be used for the composition. Preferably, each anionic vapor phase stabilizer is added to give a concentration of less than 200 parts per million (ppm). In preferred embodiments, each anionic vapor phase stabilizer is present from about 1 to 200 ppm, more preferably from about 10 to 75 ppm, even more preferably from about 10 to 50 ppm, and most preferably from 10 to 20 ppm. The amount to be used can be determined by one of ordinary skill in the art using known techniques without undue experimentation.

In embodiments, the vapor phase comprises, among other things, an anionic stabilizer that is sulfur dioxide. In embodiments, the vapor phase comprises, among other things, a stabilizer that is boron trifluoride or hydrogen fluoride. A combination of sulfur dioxide and boron trifluoride or hydrogen fluoride is preferable in some embodiments.

In embodiments, the liquid phase anionic stabilizer is a very strong acid. As used herein, a very strong acid is an acid that has an aqueous $pK_a$ of less than 1.0. Suitable very strong acidic stabilizing agents include, but are not limited to, very strong mineral and/or oxygenated acids. Examples of such very strong acids include, but are not limited to, sulfuric acid ($pK_a$—3.0), perchloric acid ($pK_a$—5), hydrochloric acid ($pK_a$—7.0), hydrobromic acid ($pK_a$—9), fluorosulfonic acid ($pK_a$<—10), chlorosulfonic acid ($pK_a$—10). In embodiments, the very strong acid liquid phase anionic stabilizer is added to give a final concentration of 1 to 200 ppm. Preferably, the very strong acid liquid phase anionic stabilizer is present in a concentration of from about 5 to 80 ppm, more preferably 10 to 40 ppm. The amount of very strong acid liquid phase anionic stabilizer to be used can be determined by one of ordinary skill in the art without undue experimentation.

Preferably, the very strong acid liquid phase anionic stabilizer is sulfuric acid, perchloric acid, or chlorosulfonic acid. More preferably, the very strong acid liquid phase anionic stabilizer is sulfuric acid.

In embodiments, sulfur dioxide is used as a vapor phase anionic stabilizer and sulfuric acid is used as a liquid phase anionic stabilizer.

The composition may also optionally include at least one other anionic stabilizing agent that inhibits polymerization. These agents are herein referred to as secondary anionic active agents to contrast them with the strong or very strong liquid phase anionic stabilizers, which are referred to hereinbelow as "primary" anionic stabilizers. The secondary anionic active agents can be included in the compositions to adjust the cure speed of the adhesive composition, for example.

The secondary anionic active agent would normally be an acid with a higher $pK_a$ than the primary anionic stabilizing agent and may be provided to more precisely control the cure speed and stability of the adhesive, as well as the molecular weight of the cured adhesive. Any mixture of primary anionic stabilizers and secondary active agents is included as long as the chemistry of the composition is not compromised and the mixture does not significantly inhibit the desired polymerization of the composition. Furthermore, the mixture should not, in medical adhesive compositions, show unacceptable levels of toxicity.

Suitable secondary anionic active agents include those having aqueous $pK_a$ ionization constants ranging from 2 to 8, preferably from 2 to 6, and most preferably from 2 to 5. Examples of such suitable secondary anionic stabilizing agents include, but are not limited to, phosphoric acid ($p_a2.2$), organic acids, such as acetic acid ($p_a4.8$), benzoic acid ($pK_a4.2$), chloroacetic acid ($pK_a2.9$), cyanoacetic acid, and mixtures thereof Preferably these secondary anionic stabilizing agents are organic acids, such as acetic acid or benzoic acid. In embodiments, the amount of acetic acid and/or benzoic acid is about 25–500 ppm. The concentration of acetic acid is typically 50–400 ppm, preferably 75–300 ppm, and more preferably 100–200 ppm. When using a stronger acid such as phosphoric acid, a concentration of 20–100 ppm, preferably 30–80 ppm, and more preferably 40–60 ppm may be utilized.

Combinations of at least one vapor phase stabilizer and at least one liquid phase anionic stabilizer are preferred. For example, combinations of sulfur dioxide and sulfuric acid, sulfur dioxide and perchloric acid, sulfur dioxide and chlorosulfonic acid, boron trifluoride and sulfuric acid, boron trifluoride and perchloric acid, boron trifluoride and chlorosulfonic acid, boron trifluoride and methanesulfonic acid, hydrogen fluoride and sulfuric acid, hydrogen fluoride and perchloric acid, hydrogen fluoride and chlorosulfonic acid, and hydrogen fluoride and methanesulfonic acid can be used. A combination of boron trifluoride, sulfur dioxide, and sulfuric acid can also be used, among other combinations. The two types of anionic stabilizers are chosen in conjunction such that the stabilizers are compatible with the chosen adhesive composition and each other stabilizer, as well as with the packaging material and the equipment used to make and package the composition. In other words, the combination of vapor phase stabilizer(s), liquid phase stabilizer(s), and monomer should be such that a stabilized, substantially unpolymerized adhesive composition is present after packaging.

Medical compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium, and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines, and hydrazide.

Suitable proteins include collagen, gelatin, casein, soybean protein, vegetable protein, keratin, and glue. The preferred protein for use in this invention is casein.

Suitable amides for use in this invention include urea, cyanamide, acrylamide, benzamide, and acetamide. Urea is a preferred amide.

Suitable alcohols include phenols, 1,4-butanediol, d-sorbitol, and polyvinyl alcohol.

Examples of suitable compounds having a b-dicarbonyl group include malonic acid, acetylacetone, ethylacetone, acetate, malonamide, diethylmalonate, or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 to Perry, which is hereby incorporated in its entirety by reference. Such heterocyclic compounds include, for example, benzimidazole, 5-methyl benzimidazole, 2-methylbenzimidazole, indole, pyrrole, 1,2,4-triazole, indoline, benzotriazole, indoline, and the like.

A preferred formaldehyde scavenger for use in this invention is sodium bisulfite.

In practicing the present invention, the formaldehyde concentration reducing agent is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form or in microencapsulated form. When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such bioerosion can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, polylactic acid, poly-1,4-dioxa-2-one, polyoxaltes, polycarbonates, copolymers of polyglycolic acid and polylactic acid, polycaprolactone, poly-b-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly(anhydrides); poly(alkyl-2-cyanoacrylates); poly(dihydropyrans); poly(acetals); poly(phosphazenes); poly(urethanes); poly(dioxinones); cellulose; and starches.

Examples of surfactants which can be added to the mineral oil include those commercially available under the designations Triton X-100™ (Rohm and Haas) (octoxynol), Tween 20™ (ICI Americas) (polysorbate), and Tween 80™ (ICI Americas) (polysorbate).

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated in its entirety by reference, discloses such cross-linking agents. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator or rate modifier may be added to initiate polymerization or to modify the rate of polymerization of the cyanoacrylate monomer/crosslinking agent blend.

The compositions of this invention may further contain fibrous reinforcement and colorants such as dyes, pigments, and pigment dyes. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2-naphthalene-sulfonic acid (FD+C Yellow No. 6); 9-(o-carboxyphenyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo- 1H-indole-5-sufonic acid disodium salt (FD+C Blue No. 2); and [phthalocyaninato (2-)] copper.

Other compositions contemplated by the present invention are exemplified by U.S. Pat. Nos. 5,624,669; 5,582,834; 5,575,997; 5,514,371; 5,514,372; and 5,259,835; and U.S. patent application Ser. No. 08/714,288, the disclosures of all of which are hereby incorporated in their entirety by reference.

EXAMPLE

In order to find a polymer (thickening agent) that is stable in both dry heat and electron beam sterilization cycles, formulations of 2-otylcyanoacrylate with several different polymers were prepared. In particular, 2-octylcyanoacrylate was mixed with one of poly(butylmethacrylate) (PBMA), poly(butylmethacrylate-co-methylmethacrylate) (PBMAMMA), poly(vinylacetate) (PVAc), and poly(2-ethylhexylmethacrylate) (PEHMA). See Tables II–V. The data in Tables II–V show that the polymers are relatively stable to the dry heat cycle at 160° C. (DH). The effect of the electron beam radiation on viscosity increases with the level of exposure. Polymer formulations exposed to 20 kGy of electron beam radiation showed less of a decrease in viscosity compared to polymer formulations exposed to 30 kGy of electron beam radiation. Therefore, the degradation of the polymer increases and the viscosity of the formulation decreases, as the exposure level increases. However, the degradation of the polymers (and thus the percentage differences) shown in Tables II–V is much less significant than the degradation of poly(2-octylcyanoacrylate) (P2OCA) shown in Table I.

TABLE II

Poly(butyl methacrylate)(PBMA)
PBMA Thickened Formulations

Viscosity (cps)

| Run # | Control | DH | % Change | 20 kGy | % Change | 30 kGy | % Change |
|---|---|---|---|---|---|---|---|
| 1 | 197 | 179 | −9.1 | 161 | −18.3 | 141 | −28.4 |
| 2 | 203 | 184 | −9.4 | 163 | −19.7 | 139 | −31.5 |
| 3 | 196 | 194 | −1.0 | 158 | −19.4 | 143 | −27.0 |
| 4 | 195 | 199 | 2.1 | 171 | −12.3 | 142 | −27.2 |
| 5 | 198 | 189 | −4.5 | 156 | −21.2 | 144 | −27.3 |
| 6 | 197 | 185 | −6.1 | 158 | −19.8 | 142 | −27.9 |
| 7 | 197 | 199 | 1.0 | 160 | −18.8 | 141 | −28.4 |
| 8 | 191 | 192 | 0.5 | 152 | −20.4 | 143 | −25.1 |

TABLE III

Poly(butyl methacrylate-co-methyl methacrylate)(PBMAMMA)
PBMAMMA Thickened Formulations Viscosity (cps)

| Run # | Control | DH | % Change | 20 kGy | % Change | 30 kGy | % Change |
|---|---|---|---|---|---|---|---|
| 1 | 205 | ND | ND | 201 | −2.0 | 186 | −9.3 |
| 2 | 196 | ND | ND | 203 | 3.6 | 185 | −5.6 |
| 3 | 198 | ND | ND | 202 | 2.0 | 189 | −4.5 |
| 4 | 198 | ND | ND | 190 | −4.0 | 184 | −7.1 |
| 5 | 194 | ND | ND | 207 | 6.7 | 183 | −5.7 |
| 6 | 196 | ND | ND | 197 | 0.5 | 185 | −5.6 |
| 7 | 199 | ND | ND | 203 | 2.0 | 186 | −6.5 |
| 8 | 207 | ND | ND | 195 | −5.8 | 187 | −9.7 |

ND means "no data".

TABLE IV

Poly(vinyl acetate)(PVAc)
PVAc Thickened Formulations

Viscosity (cps)

| Run # | Control | DH | % Change | 20 kGy | % Change | 30 kGy | % Change |
|---|---|---|---|---|---|---|---|
| 1 | 388 | 393 | 1.3 | 344 | −11.3 | 331 | −14.7 |
| 2 | 376 | 362 | −3.7 | 339 | −9.8 | 320 | −14.9 |
| 3 | 403 | 435 | 7.9 | 355 | −11.9 | 345 | −14.4 |
| 4 | 395 | 385 | −2.5 | 344 | −12.9 | 320 | −19.0 |
| 5 | 393 | 363 | −7.6 | 363 | −7.6 | 311 | −20.9 |
| 6 | 404 | ND | ND | 335 | −17.1 | 314 | −22.3 |
| 7 | 392 | 396 | 1.0 | 358 | −8.7 | 329 | −16.1 |
| 8 | 396 | 376 | −5.1 | 342 | −13.6 | 317 | −19.9 |

TABLE V

Poly(2-ethylhexyl methacrylate)(PEHMA)
PEHMA Thickened Formulations

Viscosity (cps)

| Run # | Control | DH | % Change | 20 kGy | % Change | 30 kGy | % Change |
|---|---|---|---|---|---|---|---|
| 1 | 198 | 186 | −6.1 | 178 | −10.1 | 155 | −21.7 |
| 2 | 195 | 178 | −8.7 | 173 | −11.3 | 157 | −19.5 |
| 3 | 201 | 201 | 0.0 | 182 | −9.5 | 159 | −20.9 |
| 4 | 203 | 203 | 0.0 | 168 | −17.2 | 156 | −23.2 |
| 5 | 198 | 191 | −3.5 | 171 | −13.6 | 155 | −21.7 |
| 6 | 200 | 189 | −5.5 | 175 | −12.5 | 154 | −23.0 |

TABLE V-continued

Poly(2-ethylhexyl methacrylate)(PEHMA)
PEHMA Thickened Formulations

| | | | Viscosity (cps) | | | |
|---|---|---|---|---|---|---|
| Run # | Control | DH | % Change | 20 kGy | % Change | 30 kGy | % Change |
| 7 | 197 | 198 | 0.5 | 174 | −11.7 | 152 | −22.8 |
| 8 | 198 | 198 | 0.0 | 170 | −14.1 | 151 | −23.7 |

Three different monomer formulations were prepared using 2-octylcyanoacrylate (2OCA), containing a fixed sulfur dioxide content (15 ppm) and hydroquinone content 1500 pm) as the base monomer. Varying amounts of BHA, sultone and TFA as stabilizers were then added to this base monomer to provide three different stabilized monomers (see Table VI below). Each of the three stabilized monomers was then formulated with a series of several different polymers. These materials were ampoulized and exposed to dry heat and electron beam radiation sterilization cycles.

Thickened formulation controls were tested to get a baseline before exposure to any of the sterilization cycles. Samples were then exposed to either a 160° C. dry heat cycle, or 20 or 30 kGy of electron beam radiation. Samples were then tested, after exposure (t=0), to determine the effect of the sterilization cycles on the formulations. The t=0 post exposure data for the three monomer sets is shown in Tables VII–IX below.

TABLE VI

| Formulation | Sultone (ppm) | BHA (ppm) | TFA (ppm) |
|---|---|---|---|
| K1 | 1000 | 3000 | 500 |
| Q | 1500 | 3000 | 1000 |
| S | 1500 | 5000 | 5000 |

TABLE VII

Post Exposure Data (t = 0) Formulation K1
Initial Results Formulation K1
Viscosity Modified Monomers

| | | Viscosity (cps) | | | |
|---|---|---|---|---|---|
| Sample ID | Polymer | Control | Dry Heat | 20 kGy | 30 kGy |
| 1 | None | 6.6 | 6.7 | 8.4 | 9.4 |
| 2 | PBMA | 194 | 212 | 312 | 435 |
| 3 | PBMAMMA | 216 | 223 | 403 | 623 |
| 4 | PVAc | 319 | 309 | 369 | 407 |
| 5 | PEHA | 57.5 | 56 | 402 | 100 |
| 6 | PEHMA | 207 | 205 | 298 | 376 |

TABLE VIII

Post Exposure Data (t = 0) Formulation Q
Initial Results Formulation Q
Viscosity Modified Monomers

| | | Viscosity (cps) | | | |
|---|---|---|---|---|---|
| Sample ID | Polymer | Control | Dry Heat | 20 kGy | 30 kGy |
| 1 | None | 6.8 | 6.7 | 8.6 | 9.2 |
| 2 | PBMA | 197 | 215 | 317 | 433 |
| 3 | PBMAMMA | 190 | 190 | 304 | 447 |
| 4 | PVAc | 293 | 299 | 347 | 369 |

TABLE VIII-continued

Post Exposure Data (t = 0) Formulation Q
Initial Results Formulation Q
Viscosity Modified Monomers

| | | Viscosity (cps) | | | |
|---|---|---|---|---|---|
| Sample ID | Polymer | Control | Dry Heat | 20 kGy | 30 kGy |
| 5 | PEHA | 59 | 60 | 427 | 102 |
| 6 | PEHMA | 192 | 193 | 256 | 307 |

TABLE IX

Post Exposure Data (t = 0) Formulation S
Initial Results Formulation S
Viscosity Modified Monomers

| | | Viscosity (cps) | | | |
|---|---|---|---|---|---|
| Sample ID | Polymer | Control | Dry Heat | 20 kGy | 30 kGy |
| 1 | None | 6.5 | ND | 8.4 | 9.4 |
| 2 | PBMA | 203 | 214 | 298 | 374 |
| 3 | PBMAMMA | 217 | 232 | 366 | 516 |
| 4 | PVAc | 295 | 306 | 357 | 369 |
| 5 | PEHA | 54 | 54 | 74 | 88 |
| 6 | PEHMA | 207 | 207 | 309 | 350 |

The data shows that the dry heat cycle has a minimal effect on the sample formulations. As stated above, exposure to electron beam radiation has an effect on the formulation viscosity such that the viscosity increases with increasing exposure level. However, the effect appears to be formulation dependent, since there is significant variation in the viscosity change when the formulation sets are compared.

The data indicates that the chosen polymers are stable to the dry heat sterilization cycle and do not have any significant change in viscosity after exposure. Exposure of the formulations to electron beam radiation indicates that the degradation of the polymer has an effect on the formulation viscosity. A 50–100% increase in viscosity is acceptable in the thickened formulation as long as the formulation is stable and the increase is reproducible.

While the invention has been described with reference to preferred embodiments, the invention is not limited to the specific examples given, and other embodiments and modifications can be made by those skilled in the art without departing from the spirit and scope of the invention.

What is claimed is:

1. A method of treating tissue, comprising applying to said tissue a composition comprising a polymerizable 1,1-disubstituted ethylene monomer and poly(vinyl acetate).

2. The method of claim 1 wherein said monomer is at least one member selected from the group consisting of n-butyl cyanoacrylate, 2-octyl cyanoacrylate, and ethyl cyanoacrylate.

3. The method of claim 1, wherein said monomer is 2-octyl cyanoacrylate.

4. The method of claim 1, wherein said tissue is skin.

5. The method of claim 1, wherein said tissue is burned, lacerated, irritated, abraded or incised.

6. The method of claim 1, wherein said composition is applied to apposed surgically incised or traumatically lacerated tissue.

7. The method of claim 1 wherein said composition is applied to cover or dress a wound.

* * * * *